(12) United States Patent
Renn et al.

(10) Patent No.: US 10,849,831 B2
(45) Date of Patent: Dec. 1, 2020

(54) DENTAL COMPOSITION

(71) Applicant: DENTSPLY SIRONA Inc., York, PA (US)

(72) Inventors: Caroline Renn, Singen (DE); Florian Szillat, Constance (DE); Joachim E. Klee, Radolfzell (DE); Christian Scheufler, Engen (DE); Oliver Elsner, Radolfzell (DE); Thomas Tigges, Constance (DE); Mattias Worm, Singen (DE); Helmut Ritter, Wuppertal (DE); Xiaoming Jin, Middletown, DE (US)

(73) Assignee: DENTSPLY SIRONA INC., York, PA (US)

( * ) Notice: Subject to any disclaimer, the term of this patent is extended or adjusted under 35 U.S.C. 154(b) by 73 days.

(21) Appl. No.: 16/237,983

(22) Filed: Jan. 2, 2019

(65) Prior Publication Data

US 2019/0201297 A1 Jul. 4, 2019

Related U.S. Application Data

(60) Provisional application No. 62/613,241, filed on Jan. 3, 2018.

(51) Int. Cl.
| | | |
|---|---|---|
| A61K 6/889 | (2020.01) | |
| A61K 6/20 | (2020.01) | |
| A61K 6/30 | (2020.01) | |
| A61K 6/54 | (2020.01) | |
| A61K 6/62 | (2020.01) | |
| C08L 33/26 | (2006.01) | |

(52) U.S. Cl.
CPC .............. *A61K 6/889* (2020.01); *A61K 6/20* (2020.01); *A61K 6/30* (2020.01); *A61K 6/54* (2020.01); *A61K 6/62* (2020.01); *C08L 33/26* (2013.01)

(58) Field of Classification Search
None
See application file for complete search history.

(56) References Cited

U.S. PATENT DOCUMENTS

| 7,851,515 | B2 | 12/2010 | Salz et al. | |
|---|---|---|---|---|
| 2004/0266906 | A1* | 12/2004 | Klee ..................... | C08L 33/00 523/118 |
| 2007/0004820 | A1* | 1/2007 | Klee ..................... | A61K 6/889 523/109 |
| 2007/0293642 | A1 | 12/2007 | Klee et al. | |
| 2010/0041790 | A1 | 2/2010 | Moszner et al. | |
| 2013/0158157 | A1* | 6/2013 | Stelzig ................... | B05D 7/24 523/116 |

(Continued)

FOREIGN PATENT DOCUMENTS

| JP | 2005225839 A | 8/2005 |
|---|---|---|
| WO | 2003035013 A1 | 5/2003 |
| WO | 2017060527 A1 | 4/2017 |

OTHER PUBLICATIONS

PCT International Search Report, application No. PCT/US2019/012043.

(Continued)

*Primary Examiner* — Peter A Salamon
(74) *Attorney, Agent, or Firm* — Dentsply Sirona Inc.

(57) ABSTRACT

A dental composition comprising a polymerizable acidic compound of the following formula (I):

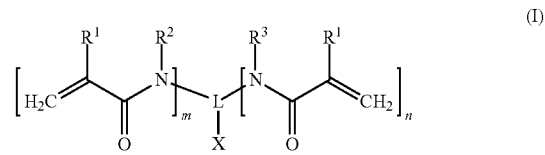

wherein $R^1$ which may be the same or different when more than one $R^1$ is present, represents a hydrogen atom or a methyl group;

$R^2$ which may be the same or different when more than one $R^2$ is present, represents a hydrogen atom, a straight-chain or branched $C_{1-6}$ alkyl group, a $C_{3-8}$ cycloalkyl group or a straight-chain or branched $C_{2-6}$ alkenyl group;

$R^3$ which may be the same or different when more than one $R^3$ is present, represents a monovalent organic moiety substituted by a group selected from —COOM, —$PO_3$M, —O—$PO_3M_2$ and —$SO_3$M, wherein M independently represents a hydrogen atom or a metal atom; or $R^2$ and $R^3$ form together a divalent organic moiety substituted by a group selected from —COOM, —$PO_3$M, —O—$PO_3M_2$ and —$SO_3$M, wherein M independently represents a hydrogen atom or a metal atom;

L represents a (m+n+1)-valent organic linker group;

X represents a hydrogen atom or a group selected from —COOM, —$PO_3$M, —O—$PO_3M_2$ or —$SO_3$M, wherein M independently is a hydrogen atom or a metal atom;

m is an integer of 0 to 6;

n is an integer of 0 to 6;

wherein (m+n) is at least 2;

provided that when n is 0, then X cannot be a hydrogen atom.

14 Claims, No Drawings

(56) References Cited

U.S. PATENT DOCUMENTS

2013/0338252 A1* 12/2013 Klee ................. A61K 6/887
 523/116
2015/0297467 A1* 10/2015 Klee ................. C09D 133/02
 523/116
2017/0296442 A1 10/2017 Renn et al.

OTHER PUBLICATIONS

PCT International Written Opinion, application No. PCT/US2019/012043.

* cited by examiner

DENTAL COMPOSITION

FIELD OF THE INVENTION

The present invention relates to a dental composition comprising a specific polymerizable acidic compound. The present invention also relates to the use of the specific polymerizable acidic compound for the preparation of a dental composition.

BACKGROUND OF THE INVENTION

Polymerizable dental compositions containing polymerizable compounds are known. Conventionally, polymerizable dental compositions are provided for a broad range of applications and must, therefore, meet a number of different requirements. For example, a polymerizable dental composition may be a dental adhesive composition, a bonding agent, a pit and fissure sealant, a dental desensitizing composition, a pulp capping composition, a dental composite, a dental glass ionomer cement, a dental cement, a dental root canal sealer composition or a dental infiltrant.

Typically, (meth)acrylates are used as polymerizable components in polymerizable dental compositions due to their excellent reactivity in radical polymerizations. In order to provide crosslinking capability, polyfunctional (meth) acrylates such as bis-GMA, were extensively used. EP 2 895 138 A1 discloses polymerizable dental compositions comprising N-substituted acrylic acid amide compounds. EP15 178 515 and EP 15 188 969 disclose N,N'-diallyl-1,4-bisacrylamido-(2E)-but-2-en (BAABE).

Dental restorative materials are dental compositions which are known for restoring the function, morphology and integrity of dental structures damaged by physical damage or caries-related decay of enamel and/or dentin. Dental restorative materials are required to have high biocompatibility, good mechanical properties and mechanical and chemical resistance over a long period of time.

Dental restorative materials include glass ionomer cements having good biocompatibility and good adhesion to the dental hard tissues. Moreover, glass ionomer cements may provide cariostatic properties through the release of fluoride ions. Glass ionomer cements are cured by an acid-base reaction between a reactive glass powder and a polyalkenoic acid. However, conventional glass ionomer cements have a relatively low flexural strength and are brittle due to salt-like structures between the polyacid and the basic glass.

The mechanical properties of glass ionomer cements may be improved by the selection of a polymerizable compounds in the aqueous dental glass ionomer composition.

WO 03/011232 A1 discloses water-based dental glass ionomer cements which may contain α,β-unsaturated monomers selected from the group consisting of water-soluble, water-miscible or water-dispersible acrylates and methacrylates such as 2-hydroxyethyl methacrylate, 2-hydroxypropyl methacrylate, tetrahydrofurfuryl methacrylate, glycerol mono- or di-methacrylate, trimethylol propane trimethacrylate, ethylene glycol dimethacrylate, polyethylene glycol dimethacrylate, urethane methacrylates, acrylamide, methacrylamide, diacetone acrylamide, methacrylamide, glycerol phosphate monomethacrylates, glycerol phosphate dimethacrylates, hydroxyethyl methacrylate phosphates and citric acid di- or tri-methacrylates.

SUMMARY OF THE INVENTION

It is a problem of the present invention to provide a dental composition comprising a specific polymerizable compound which is copolymerizable with conventional (meth)acrylates, (meth)acrylamides and allylic ethers, and which has a favorable polymerization enthalpy, good solubility in water and/or in an acidic environment and biocompatibility.

Moreover, it is a problem of the present invention to provide a specific polymerizable compound which may be used in a dental composition.

The problem of the invention is solved according to the claims. Accordingly, the present invention provides a dental composition comprising a polymerizable acidic compound of the following formula (I):

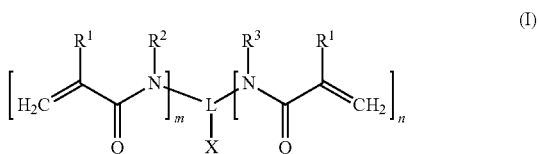

wherein $R^1$ which may be the same or different when more than one $R^1$ is present, represents a hydrogen atom or a methyl group;

$R^2$ which may be the same or different when more than one $R^2$ is present, represents a hydrogen atom, a straight-chain or branched $C_{1-6}$ alkyl group, a $C_{3-8}$ cycloalkyl group or a straight-chain or branched $C_{2-6}$ alkenyl group;

$R^3$ which may be the same or different when more than one $R^3$ is present, represents a monovalent organic moiety substituted by a group selected from —COOM, —$PO_3M$, —O—$PO_3M_2$ and —$SO_3M$, wherein M independently represents a hydrogen atom or a metal atom; or $R^2$ and $R^3$ form together a divalent organic moiety substituted by a group selected from —COOM, —$PO_3M$, —O—$PO_3M_2$ and —$SO_3M$, wherein M independently represents a hydrogen atom or a metal atom;

L represents a (m+n+1)-valent organic linker group;

X represents a hydrogen atom or a group selected from —COOM, —$PO_3M$, —O—$PO_3M_2$ or —$SO_3M$, wherein M independently is a hydrogen atom or a metal atom;

m is an integer of 0 to 6;

n is an integer of 0 to 6;

wherein (m+n) is at least 2;

provided that when n is 0, then X cannot be a hydrogen atom.

Moreover, the present invention provides a use of the polymerizable acidic compound of the formula (I) for the preparation of a dental composition.

The present invention is based on the recognition that a polymerizable acidic compound of the formula (I) has excellent polymerization enthalpy. Moreover, the present invention is based on the recognition that the viscosity of the compounds of formula (I) is within the range of (meth) acrylates typically applied in the field of dental compositions. In addition, the polymerizable compound of formula (I) provides an advantageous maximum rate of polymerization and desirable mechanical characteristics such as flexural strength. Furthermore, the polymerizable acids are soluble in water or in aqueous acidic formulations. When used in a dental glass ionomer cement composition, the one or more acidic groups of the compound of formula (I) may take part in the cement reaction and thereby provides an additional curing mechanism.

DETAILED DESCRIPTION OF PREFERRED EMBODIMENTS

The terms "polymerization" and "polymerizable" relates to the combining or the capability to combine by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as polymer networks. In case of a higher conversion rate of the polymerizable monomer, the amount of multifunctional monomers may be reduced or the leaching problem may be alleviated.

The terms "curing" and "photocuring" mean the polymerization of functional oligomers and monomers, or even polymers, into a crosslinked polymer network and/or the hardening of a composition in a cement reaction. For example, curing may be the polymerization of unsaturated monomers or oligomers in the presence of crosslinking agents.

"Actinic radiation" is any electromagnetic radiation that is capable of producing photochemical action and can have a wavelength of at least 150 nm and up to and including 1250 nm, and typically at least 300 nm and up to and including 750 nm.

The term "photoinitiator" is any chemical compound that forms free radicals when activated, e.g. by exposure to actinic light or interaction with a coinitiator in a photochemical process.

The term "coinitiator" refers to a molecule that produces a chemical change in another molecule such as a photoinitiator in a photochemical process. The coinitiator may be a photoinitiator or an electron donor.

The term "electron donor" as used herein means a compound which is capable of donating electrons in a photochemical process. Suitable examples include organic compounds having heteroatoms with electron lone pairs, for example amine compounds.

The term "polyacidic polymer" means that the polymer has a plurality of acidic groups, preferably carboxylic acid groups, which may participate in a cement reaction with a reactive glass. The carboxylic acid groups are preferably present in the backbone and derived from acrylic acid, methacrylic acid and/or itaconic acid.

The "straight-chain or branched $C_{1-6}$ alkyl group" and "straight-chain or branched $C_{2-6}$ alkenyl group" is not particularly limited. Preferably, the "straight-chain or branched $C_{1-6}$ alkyl group" and "straight-chain or branched $C_{2-6}$ alkenyl group" represents a straight chain $C_{1-4}$ alkyl group or a straight chain $C_{2-4}$ alkenyl group. The "$C_{3-8}$ cycloalkyl group" is not particularly limited. Preferably, the "$C_{3-8}$ cycloalkyl group" is a $C_{3-6}$ cycloalkyl group.

Illustrative examples for straight chain or branched alkyl groups are methyl, ethyl, n-propyl, i-propyl, n-butyl, isobutyl, tert-butyl, sec-butyl, pentyl or hexyl, and for the straight chain or branched alkenyl group ethenyl, n-propenyl, i-propenyl, n-butenyl, isobutenyl, tert-butenyl sec-butenyl, pentenyl or hexenyl.

The term "alkenyl" means a monovalent group derived from a hydrocarbon having the above defined carbon number. This alkenyl group preferably contains at least one carbon-carbon double bond, more preferably 1 to 3 carbon-carbon double bonds, even more preferably 1 or 2 carbon-carbon double bonds, most preferably one carbon-carbon double bond. Furthermore, it is preferred that at least one carbon-carbon double bond of the alkenyl group is located between second and third carbon atoms adjacent to a first carbon which attaches the alkenyl group to compound of formula (I).

The present invention provides a dental composition. The dental composition may be a dental restorative or dental prosthetic composition. Preferably, the dental composition is selected from a dental adhesive composition, a dental composite composition, a resin modified dental cement, a pit and fissure sealer, a desensitizer and a varnish.

The dental composition of the present invention comprises a specific polymerizable acidic compound of the following formula (I):

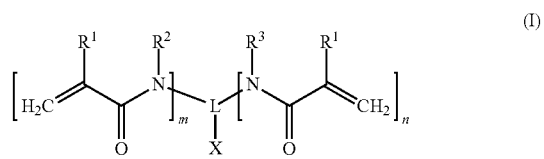

In formula (I), $R^1$ which may be the same or different when more than one $R^1$ is present, represents a hydrogen atom or a methyl group. Preferably, $R^1$ represents a hydrogen atom.

In formula (I), $R^2$ which may be the same or different when more than one $R^2$ is present, represents a hydrogen atom, a straight-chain or branched $C_{1-6}$ alkyl group, a $C_{3-8}$ cycloalkyl group or a straight-chain or branched $C_{2-6}$ alkenyl group. According to a preferred embodiment, $R^2$ represents a hydrogen atom, a $C_{1-6}$ alkyl group, or a $C_{2-6}$ alkenyl group. According to a more preferred embodiment, $R^2$ is selected from a hydrogen atom, a methyl group, an ethyl group, an iso-propyl group, an n-propyl group, and an ally group.

In formula (I), $R^3$ which may be the same or different when more than one $R^3$ is present, represents a monovalent organic moiety substituted by a group selected from —COOM, —$PO_3M$, —O—$PO_3M_2$ and —$SO_3M$, wherein M independently represents a hydrogen atom or a metal atom. The monovalent organic moiety is preferably an organic moiety having from 1 to 20 carbon atoms, more preferably 2 to 10 carbon atoms. The organic moiety may contain heteroatoms selected from oxygen atoms, sulfur atoms and nitrogen atoms in the main chain thereof. Specifically, the organic moiety may contain linkages such as ether, ester, thioether, amide, urea or urethane linkages. The monovalent organic moiety is linked to the nitrogen atom by a covalent single bond. The organic moiety may be further substituted by a group other than a —COOM, —$PO_3M$, —O—$PO_3M_2$ and —$SO_3M$, wherein M is as defined above. For example, the organic moiety may be substituted by 1 to 5 groups selected from hydroxyl groups, thiol groups, keto groups, and halogen atoms such as fluorine.

According to a specific embodiment of the compound of formula (I), $R^2$ and $R^3$ may form together a divalent organic moiety substituted by a group selected from —COOM, —$PO_3M$, —O—$PO_3M_2$ and —$SO_3M$, wherein M independently represents a hydrogen atom or a metal atom.

The divalent organic moiety is preferably an organic moiety having from 1 to 20 carbon atoms, more preferably 2 to 10 carbon atoms. The organic moiety may contain heteroatoms selected from oxygen atoms, sulfur atoms and nitrogen atoms in the main chain thereof. Specifically, the divalent organic moiety may contain linkages such as ether, ester, thioether, amide, urea or urethane linkages. The divalent organic moiety is linked to the nitrogen atoms by covalent single bonds. The divalent organic moiety may be further substituted by a group other than a —COOM, —PO$_3$M, —O—PO$_3$M$_2$ and —SO$_3$M, wherein M is as defined above. For example, the organic moiety may be substituted by 1 to 5 groups selected from hydroxyl groups, thiol groups, keto groups, and halogen atoms such as fluorine.

Preferably, R$^3$ is a group of the following formula (II):

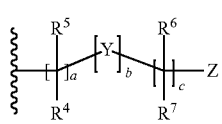

wherein
R$^4$ which may be the same or different when more than one R$^4$ is present, represents a hydrogen atom or a C$_{1-4}$ alkyl group;
R$^5$ which may be the same or different when more than one R$^5$ is present, represents a hydrogen atom or a C$_{1-4}$ alkyl group;
R$^6$ which may be the same or different when more than one R$^6$ is present, represents a hydrogen atom or a C$_{1-4}$ alkyl group;
R$^7$ which may be the same or different when more than one R$^7$ is present, represents a hydrogen atom or a C$_{1-4}$ alkyl group;
Y represents an oxygen atom or a sulfur atom;
Z represents a group selected from —COOM, —PO$_3$M, —O—PO$_3$M$_2$ or —SO$_3$M, wherein M independently is a hydrogen atom or a metal atom;
a is an integer of 1 to 6;
b is an integer of 0 or 1; and
c is an integer of 1 to 6.

According to a preferred embodiment, R$^4$, R$^5$, R$^6$, and R$^7$ represent a hydrogen atom.

In formula (I), L represents a (m+n+1)-valent organic linker group.

The organic linker group is preferably an organic moiety having from 1 to 20 carbon atoms, more preferably 2 to 10 carbon atoms. The organic linker group may contain heteroatoms selected from oxygen atoms, sulfur atoms and nitrogen atoms in the main chain thereof. Specifically, the organic moiety may contain linkages such as ether, ester, thioether, amide, urea or urethane linkages. The monovalent organic moiety is linked to the nitrogen atom by a covalent single bond. The organic moiety may be further substituted by a group other than a —COOM, —PO$_3$M, —O—PO$_3$M$_2$ and —SO$_3$M, wherein M is as defined above. For example, the organic moiety may be substituted by 1 to 5 groups selected from hydroxyl groups, thiol groups, keto groups, and halogen atoms such as fluorine. According to a preferred embodiment, L represents a (m+n+1)-valent aliphatic or alicyclic linker group.

In formula (I), X represents a hydrogen atom or a group selected from —COOM, —PO$_3$M, —O—PO$_3$M$_2$ or —SO$_3$M, wherein M independently is a hydrogen atom or a metal atom. According to a preferred embodiment, X represents a group selected from —COOM, —PO$_3$M, —O—PO$_3$M$_2$, wherein M is a hydrogen atom. According to a preferred embodiment, X is a hydrogen atom.

In formula (I), m is an integer of 0 to 6. According to a specific embodiment, m is 0. According to a further specific embodiment, m is 1. According to a further specific embodiment, m is 2. Preferably, m is 0 to 2.

In formula (I), n is an integer of 0 to 6. According to a specific embodiment, n is 0. According to a further specific embodiment, n is 1. According to a further specific embodiment, n is 2. Preferably, n is 0 to 2.

In formula (I), (m+n) is at least 2. According to a specific embodiment, m is 0 and n is 2. According to a further specific embodiment, m is 1 and n is 1. According to a further specific embodiment, m is 2 and n is 0.

In formula (I), provided that when n is 0, then X cannot be a hydrogen atom. Accordingly, a compound of formula (I) is a compound which always contains an acidic group selected from —COOM, —PO$_3$M, —O—PO$_3$M$_2$ or —SO$_3$M, wherein M independently is a hydrogen atom or a metal atom.

The compound of the formula (I) is preferably contained in a dental composition according to the present invention in an amount of from 1 to 70 percent by weight based on the total weight of the dental composition. More preferably, the dental composition contains 5 to 50 percent by weight based on the total weight of the dental composition of the compound of formula (I).

The dental composition according to the present invention may further comprise a solvent and/or a particulate filler.

Use of a polymerizable acidic compound of the following formula (I):

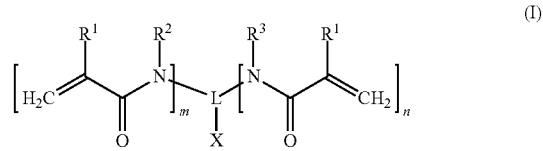

wherein
R$^1$ which may be the same or different when more than one R$^1$ is present, represents a hydrogen atom or a methyl group;
R$^2$ which may be the same or different when more than one R$^2$ is present, represents a hydrogen atom, a straight-chain or branched C$_{1-6}$ alkyl group, a C$_{3-8}$ cycloalkyl group or a straight-chain or branched C$_{2-6}$ alkenyl group;
R$^3$ which may be the same or different when more than one R$^3$ is present, represents a monovalent organic moiety substituted by a group selected from —COOM, —PO$_3$M, —O—PO$_3$M$_2$ and —SO$_3$M, wherein M independently represents a hydrogen atom or a metal atom; or
R$^2$ and R$^3$
form together a divalent organic moiety substituted by a group selected from —COOM, —PO$_3$M, —O—PO$_3$M$_2$ and —SO$_3$M, wherein M independently represents a hydrogen atom or a metal atom;
L represents a (m+n+1)-valent organic linker group;
X represents a hydrogen atom or a group selected from —COOM, —PO$_3$M, —O—PO$_3$M$_2$ or —SO$_3$M, wherein M is a hydrogen atom or a metal atom;
m is an integer of 0 to 6;
n is an integer of 0 to 6;
wherein m+n is at least 2;

provided that when n is 0, then X cannot be a hydrogen atom, for the preparation of a dental composition.

The dental composition may be selected from a dental adhesive composition, a dental composite composition, a resin modified dental cement, a pit and fissure sealer, a desensitizer and a varnish.

According to a preferred embodiment, the dental composition is an aqueous resin modified dental glass ionomer composition, which preferably comprises
(A) a reactive particulate glass,
(B) a water-soluble comprising acidic groups, which is reactive with the particulate glass in a cement reaction, and preferably having polymerizable groups;
(C) a polymerizable resin containing the polymerizable acidic compound of the formula (I) according to the present invention; and
(D) a polymerization initiator system.

The term "reactive particulate glass" refers to a solid mixture of mainly metal oxides transformed by a thermal melt process into a glass and crushed by various processes, which glass is capable of reacting with a polymer containing acidic groups in a cement reaction. The glass is in particulate form. Moreover, the reactive particulate glass may be surface modified, e.g. by silanation or acid treatment. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable particulate reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

Preferably, the reactive particulate glass according to (A) is a reactive particulate glass comprising:
1) 20 to 45% by weight of silica,
2) 20 to 40% by weight of alumina,
3) 20 to 40% by weight of strontium oxide,
4) 1 to 10% by weight of P2O5, and
5) 3 to 25% by weight of fluoride.

The present aqueous dental glass ionomer composition preferably comprises 20 to 90 percent by weight of the reactive particulate glass, more preferably 30 to 80 percent by weight, based on the total weight of the composition.

The reactive particulate glass usually has an average particle size of from 0.005 to 100 μm, preferably of from 0.01 to 40 μm as measured, for example, by electron microscopy or by using a conventional laser diffraction particle sizing method as embodied by a MALVERN Mastersizer S or MALVERN Mastersizer 2000 apparatus.

The reactive particulate glass may have a unimodal or multimodal (e.g., bimodal) particle size distribution, wherein a multimodal reactive particulate glass represents a mixture of two or more particulate fractions having different average particle sizes. [0029] The reactive particulate glass may be a an agglomerated reactive particulate glass which is obtainable by agglomerating a reactive particulate glass in the presence of a modified polyacid and/or polymerizable (meth)acrylate resins. The particle size of the agglomerated reactive particulate glass may be adjusted by suitable size-reduction processes such as milling.

The reactive particulate glass may be surface modified by a component according to (B), (C) and/or (D). In particular, the reactive particulate glass may be surface modified by one or more components of the polymerization initiator system (D) in order to avoid contact of the one or more components of the polymerization initiator system (D) with an acid under aqueous conditions.

The reactive particulate glass may alternatively or additionally be surface modified by a surface modifying agent. Preferably, the surface modifying agent is a silane. A silane provides a suitable hydrophobicity to the reactive particulate glass, which allows for an advantageous, homogeneous admixture with the organic components according to (B), (C) and (D) of the aqueous dental glass ionomer composition.

The water-soluble polymer comprising acidic groups and preferably having polymerizable groups, is an organic polymeric compound comprising ionizable pendant groups, such as carboxylic acid groups. The carboxylic acid groups of the polymer are capable of reacting with a reactive particulate glass in a cement reaction to form a glass ionomer cement.

The water-soluble polymer comprising acidic groups according to (B) is obtainable by a process comprising a copolymerization step a), a coupling step b), and an optional deprotection step.

The term "water-soluble" used in the context with the term "polymerizable polymer" means that at least 0.1 g, preferably 0.5 g of the polymerizable polymer dissolves in 100 g of water at 20° C.

The term "polymer having polymerizable groups" used in the context with component (B) refers to a polymer containing one or more polymerizable moieties capable of polymerizing and crosslinking the polymer for improving the mechanical properties and the long-term mechanical and chemical resistance of the cured aqueous dental glass ionomer composition.

The water-soluble polymer according to (B) is preferably hydrolysis-stable, which means that the polymer is stable to hydrolysis in an acidic medium, such as in a dental composition. Specifically, the polymer does not contain groups such as ester groups which hydrolyse in aqueous media at pH 3 at room temperature within one month.

A preferred water-soluble, polymer comprising acidic groups, and preferably having polymerizable groups according to (B) is obtainable by a process comprising step a) of copolymerizing a mixture comprising (i) a first copolymerizable monomer comprising at least one optionally protected carboxylic acid group and a first polymerizable organic moiety and (ii) a second copolymerizable monomer comprising one or more optionally protected primary and/or secondary amino groups and a second polymerizable organic moiety for obtaining an amino group containing copolymer. The mixture may also contain further monomers.

The first copolymerizable monomer to be used in step a) comprises at least one, preferably one to three, more preferably one or two, most preferably one optionally protected carboxylic acid group(s).

The protecting group of an optionally protected carboxylic acid group is not particularly limited as long as it is a carboxyl-protecting group known to those of ordinary skill in the art of organic chemistry (cf. P. G. M. Wuts and T. W. Greene, Greene's Protective Groups in Organic Synthesis, 4th Edition, John Wiley and Sons Inc., 2007). Preferably, the carboxyl-protecting group is selected from a trialkylsilyl group, an alkyl group and an arylalkyl group. More preferably, the carboxyl-protecting group is selected from an alkyl group or an arylalkyl group. Most preferably, the carboxyl-protecting group is selected from a tert-butyl group and a benzyl group. In one preferred embodiment, the carboxyl-protecting group is a tert-butyl group.

The term "polymerizable organic moiety" as used herein means an organic moiety of a molecule which can be used to covalently link this molecule in a chemical reaction (polymerization) to other molecules reactive with this moiety to form a macromolecule of repeating or alternating structural units. Preferably, this polymerizable organic moiety is a carbon-carbon double bond as in the case of an ethylenically unsaturated moiety.

In a preferred embodiment, the first copolymerizable monomer is represented by the general formula (1):

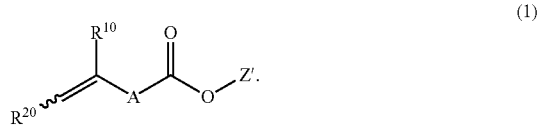

(1)

In formula (1), $R^{10}$ is a hydrogen atom, a —COOZ group or a straight chain or branched $C_{1-6}$ alkyl group which may be substituted by a —COOZ group. Preferably, $R^{10}$ is a hydrogen atom, a —COOZ group or a methyl group. More preferably, $R^{10}$ is a hydrogen atom or a methyl group.

In formula (1), $R^{20}$ is a hydrogen atom, a —COOZ' group or a straight-chain or branched $C_{1-6}$ alkyl group which may be substituted by a —COOZ' group. Preferably, $R^{20}$ is a hydrogen atom or a —COOZ' group. More preferably, $R^{20}$ is a hydrogen atom. In formula (1), the dotted line indicates that $R^{20}$ may be in either the cis or trans orientation.

In formula (1), A is a single bond or a straight-chain or branched $C_{1-6}$ alkylene group which group may contain 1 to 3 heteroatoms in between two carbon atoms of the alkylene carbon chain, which heteroatoms are selected from an oxygen atom, nitrogen atom, and sulfur atom, and/or which alkylene group may contain in between two carbon atoms of the alkylene carbon chain 1 to 3 groups selected from an amide bond or a urethane bond. Preferably, A is a single bond or a straight-chain or branched $C_{1-6}$ alkylene group which group may contain a heteroatom in between two carbon atoms of the alkylene carbon chain, which heteroatom is selected from an oxygen atom or a nitrogen atom, and/or which alkylene group may contain in between two carbon atoms of the alkylene carbon chain a group selected from an amide bond or a urethane bond. More preferably, A is a single bond or a straight-chain $C_{1-6}$ alkylene group. Most preferably, A is a single bond.

In formula (1), Z' which may be the same or different independently represents a hydrogen atom, a metal ion, a protecting group for a carboxylic acid group, or the Z' forms with a further —COOZ' group present in the molecule an intramolecular anhydride group. The metal ion may be a monovalent metal ion such as an alkali metal ion. In one embodiment, Z' is a protecting group for a carboxylic acid group. In another embodiment, Z' is a hydrogen atom. When Z' forms with a further —COOZ' group present in the molecule an intramolecular anhydride group (—C(O)OC(O)—), the further —COOZ' group may be preferably present on $R^1$ such as in case of itaconic acid anhydride.

In a preferred embodiment, Z' is a hydrogen atom and the polymerization reaction is conducted in an alkaline environment. In an alternative preferred embodiment, Z' is a hydrogen atom and the amino groups of the first copolymerizable monomer and of the second copolymerizable monomer carry a protecting group.

Preferably, the first copolymerizable monomer is a protected (meth)acrylic acid monomer. More preferably, a first polymerizable monomer is selected from tert-butyl acrylate and benzyl acrylate. Most preferably, a first polymerizable monomer is tert-butyl acrylate.

In a preferred embodiment of the aqueous dental glass ionomer composition of the present invention, the second copolymerizable monomer is represented by the general formula (2):

(2)

In formula (2), $R^{30}$ is a hydrogen atom or a straight chain or branched $C_{1-6}$ alkyl group which may be substituted by a —COOZ' group. Preferably, $R^{30}$ is a hydrogen atom. In formula (2), the dotted line indicates that $R^{30}$ may be in either the cis or trans orientation.

In formula (2), X' is a protected amino group or a hydrocarbon group having 1 to 20 carbon atoms, which is substituted with an amino group which may carry a protecting group, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ', amino groups, hydroxyl groups and thiol groups. Preferably, X' is a hydrocarbon group having 1 to 20 carbon atoms, which is substituted with an amino group which may carry a protecting group, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ' group. More preferably, X' is a hydrocarbon group having 1 to 20 carbon atoms, even more preferably 1 to 6 carbon atoms, which is substituted with an amino group which may carry a protecting group, wherein the hydrocarbon group may contain an oxygen atom and/or which hydrocarbon group may contain an amide bond and which hydrocarbon group may further be substituted with a —COOZ' group. In as specific embodiment wherein X is a protected amino group, the compound of formula (2) is allyl amine, wherein the amino group carries a protecting group.

The protecting group of a protected amino group or an optionally protected amino group is not particularly limited and may be any conventional protecting group for an amino group as, for example, described in P. G. M. Wuts and T. W. Greene, Greene's Protective Groups in Organic Synthesis, 4th Edition, John Wiley and Sons Inc., 2007. Preferably, the amino-protecting group is selected from an acyl group, an arylalkyl group, an alkoxy carbonyl group, and an aryloxycarbonyl group. More preferably, the amino-protecting group is an acyl group. Most preferably, the amino-protecting group is a formyl group.

In formula (2), Y' is a hydrogen atom or a hydrocarbon group having 1 to 20 carbon atoms, wherein the hydrocarbon group may contain 1 to 6 heteroatoms, which heteroatoms are selected from an oxygen atom, nitrogen atom, and sulfur atom, and/or which hydrocarbon group may contain a group selected from an amide bond or a urethane bond and which hydrocarbon group may further be substituted with up to 6 groups selected from —COOZ", amino groups, hydroxyl groups and thiol groups. Preferably, Y is a hydrogen atom or a hydrocarbon group having 1 to 20 carbon atoms, wherein the hydrocarbon group may contain a heteroatom, which heteroatom is selected from an oxygen atom and a nitrogen atom, and/or which hydrocarbon group may contain a group selected from an amide bond or a urethane bond and which hydrocarbon group may further be substituted with a —COOZ" group. More preferably, Y' is a hydrogen atom or a hydrocarbon group having 1 to 20 carbon atoms, even more preferably 1 to 6 carbon atoms, wherein the hydrocarbon group may contain an oxygen atom and/or which hydrocarbon group may contain an amide bond and which hydrocarbon group may further be substituted with a —COOZ" group. In one preferred embodiment, Y is a hydrogen atom.

In formula (2), Z" which may be the same or different, independently represents a hydrogen atom, a metal ion, a protecting group for a carboxylic acid group, or the Z" forms with a further —COOZ" group present in the molecule an intramolecular anhydride group. In one embodiment, Z" is a protecting group for a carboxylic acid group. In another embodiment, Z" is a hydrogen atom. The metal ion may be a monovalent metal ion such as an alkali metal ion. In another embodiment, Z" is a hydrogen atom. When Z' forms with a further —COOZ" group present in the molecule an intramolecular anhydride group (—C(O)OC(O)—).

In a preferred embodiment, Z" is a hydrogen atom and the polymerization reaction is conducted in an alkaline environment. In an alternative preferred embodiment, Z" is a hydrogen atom and the amino groups of the second copolymerizable monomer carry a protecting group.

In one embodiment, the second copolymerizable monomer comprises a second copolymerizable organic moiety selected from the group of (meth)acrylamide moieties which may be substituted and substituted (meth)acrylic acid which may be protected. In another embodiment, the second copolymerizable monomer is selected from allyl amine, aminopropyl vinyl ether, aminoethyl vinyl ether, N-vinyl formamide and 2-aminomethyl acrylic acid. In a preferred embodiment, the second copolymerizable monomer is aminopropyl vinyl ether. The amino group may be in the form of an ammonium salt such as a ammonium chloride. Preferred structures wherein the amino group may also carry a protecting group are depicted in Scheme 1 below.

Scheme 1

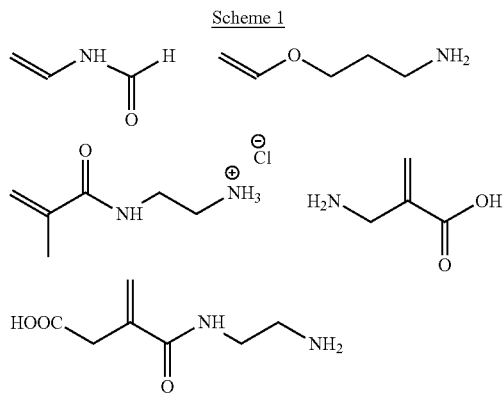

-continued

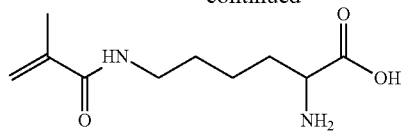

The molar ratio of first copolymerizable monomer to second copolymerizable monomer in the mixture copolymerized in step a) (mol first copolymerizable monomer/mol second copolymerizable monomer) is preferably in the range of from 100:1 to 100:50, more preferably in the range from 100:2 to 100:20, still more preferably in a range from 100:3 to 100:10.

The further copolymerizable monomers optionally to be used in step a) comprise at least one, preferably one to three, more preferably one or two, most preferably one optionally protected acidic group(s) which are not carboxylic acid groups. Specific examples of acidic groups are sulfonic acid groups (—SO$_3$M'), phosphonic acid groups (—PO$_3$M'$_2$) or phosphoric acid ester groups (—OPO$_3$M'$_2$), or salts thereof, wherein M' may independently be a hydrogen atom or a monovalent ion such as an alkali metal or an ammonium ion.

Specific examples of the optional further monomers are selected from 2-acrylamido-2-methylpropane sulfonic acid, vinyl phosphonate, and vinyl sulfonic acid.

In a preferred embodiment, the solutions containing the first copolymerizable monomer and the second copolymerizable monomer are separately saturated with nitrogen before combining them for copolymerization to minimize possible side-products of a competitive Aza-Michael addition.

Step a) of the aqueous dental glass ionomer composition proceeds as a chain-growth polymerization. In one embodiment, step a) comprises radical copolymerization.

The type of copolymer formed by step a) of the present invention may be a statistical copolymer, a random copolymer, an alternating copolymer, a block copolymer or a combination thereof.

A copolymer obtained by step a) of the present invention is an amino group containing copolymer, such as, for example, a copolymer obtainable by copolymerization of acrylate and aminopropyl vinyl ether.

The reaction conditions of the polymerization reaction according to step a) of the present invention are not particularly limited. Accordingly, it is possible to carry out the reaction in the presence or absence of a solvent. A suitable solvent may be selected from the group of water, dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction is preferably carried out in the presence of a polymerization initiator. In a preferred embodiment of the aqueous dental glass ionomer composition, the polymerization initiator is selected from azobisisobutyronitrile (AIBN), 2,2-azobis(2-amidinopropane)dihydrochloride, 2,2'-azobis (2-methylbutyronitrile), 2,2'-azobis(N,N'-dimethyleneisobutyramidine) dihydrochloride, and 4,4'-azobis(4-cyano pentanoic acid). The amount of the polymerization initiator is not particularly limited. Suitably, the amount is in the range of from 0.001 to 5 mol % based on the total amount of the monomers.

The reaction product obtained in step a) may be isolated by precipitation and filtration, or lyophilization. The product may be purified according to conventional methods.

Step b) of the aqueous dental glass ionomer composition is a step of coupling a compound having a polymerizable moiety and a functional group reactive with an amino group of repeating units derived from the second copolymerizable monomer in the amino group containing copolymer obtained in the first step wherein the optionally protected amino group is deprotected.

Preferably, the coupling reaction in step b) is an addition reaction or a condensation reaction forming a bond selected from an amide bond, a urea bond or a thiourea bond.

The term "functional group reactive with an amino group" as used herein means any group which can form a covalent bond with an amino group of the amino group containing copolymer. Preferably, a functional group reactive with an amino group is a carboxylic acid group or a derivative thereof such as an ester group or an anhydride thereof, an isocyanate group or an isothiocyanate group. More preferably, a functional group reactive with an amino group is a carboxylic acid group or a derivative thereof.

If the amino group of repeating units derived from the second copolymerizable monomer in the amino group containing copolymer obtained in the first step is protected, the amino group can be deprotected prior to step b) or concomitant with step b).

The conditions for deprotection of an optionally protected amino group are selected according to the protecting group used. Preferably, the protected amino group is deprotected by hydrogenolysis or treatment with acid or base.

If the deprotection of a protected amino group is carried out concomitantly with step b), it will be understood by a person skilled in the art that the deprotection conditions and the conditions for step b) have to be selected so that both reactions can proceed efficiently.

In a preferred embodiment of the aqueous dental glass ionomer composition, the compound having a polymerizable moiety and a functional group reactive with an amino group of repeating units derived from the second copolymerizable monomer is a compound represented by the general formula (3):

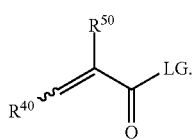

(3)

In formula (3), $R^{40}$ is a hydrogen atom or a straight chain or branched $C_{1-6}$ alkyl group which may be substituted by a —COOZ'' group, and $R^{50}$ is a hydrogen atom or a straight-chain or branched $C_{1-6}$ alkyl group which may be substituted by a —COOZ''' group. Preferably, $R^{40}$ is a hydrogen atom, and $R^{50}$ is a hydrogen atom or a methyl group. More preferably, $R^{40}$ is a hydrogen atom, and $R^{50}$ is a methyl group. In formula (3), the dotted line indicates that $R^{40}$ may be in either the cis or trans orientation.

In formula (3), Z''' which may be same or different, independently represents a hydrogen atom, a metal ion, a protecting group for a carboxylic acid group, or the Z''' forms with a further —COOZ''' group present in the molecule an intramolecular anhydride group.

In one embodiment, Z''' is a protecting group for a carboxylic acid group. In another embodiment, Z''' is a hydrogen atom. In a preferred embodiment, Z''' is a hydrogen atom and the polymerization reaction is conducted in an alkaline environment. In an alternative preferred embodiment, Z''' is a hydrogen atom and the amino groups of the second copolymerizable monomer carry a protecting group.

In one embodiment, in formula (3), LG is a leaving group. Preferably, LG is a chlorine atom or a bromine atom, or forms with the adjacent carbonyl group a carboxylic acid anhydride moiety. More preferably, LG is a group which is suitable for reacting the compound of formula (3) in a Schotten-Baumann type reaction.

In another embodiment, LG may replace Z''' and form with $R^{40}$ or $R^{50}$ an intramolecular carboxylic acid anhydride group.

In yet another embodiment two molecules of formula (3) form an intermolecular carboxylic acid anhydride group by sharing a common LG, wherein LG is an oxygen atom.

It is particularly preferred that the compound of formula (3) is acrylic acid, (meth)acrylic acid, crotonic acid, isocrotonic acid, tiglic acid, angelic acid, or an anhydride of the aforementioned acids formed of two identical or different acids; more preferably an anhydride of the aforementioned acids formed of two identical acids. Most preferably, the compound of formula (3) is (meth)acrylic anhydride.

The coupling according to step b) of the present invention serves to introduce one or more polymerizable moieties into the amino group containing copolymer, which moieties can be post-polymerized to provide additional covalent and advantageously also ionic crosslinking, imparting additional strength to the dental material.

In one embodiment of the aqueous dental glass ionomer composition, the carboxylic acid groups of the copolymer obtained in step b) are not protected and the copolymer can be used as a polymer according to the present invention without further treatment. In an alternative embodiment, the carboxylic acid groups of the copolymer obtained in step b) are protected and the carboxylic acid groups have to be deprotected before the copolymer exhibits the features of a polymer according to the present invention.

The reaction conditions of the reaction according to step b) of the present invention are not particularly limited. Accordingly, it is possible to carry out the reaction in the presence or absence of a solvent. A suitable solvent may be selected from the group of dimethyl formamide (DMF), tetrahydrofurane (THF), and dioxane.

The reaction temperature is not particularly limited. Preferably, the reaction is carried out at a temperature of between −10° C. to the boiling point of the solvent. Preferably, the reaction temperature is in the range of from 0° C. to 80° C.

The reaction time is not particularly limited. Preferably the reaction time is in the range of from 10 minutes to 48 hours, more preferably 1 hour to 36 hours.

The reaction product obtained in step b) may be isolated by precipitation and filtration. The product may be purified.

The aqueous dental glass ionomer composition optionally includes a step of deprotecting the protected carboxylic acid group after step a) or step b), for obtaining a polymerizable polymer. In a preferred embodiment, the aqueous dental glass ionomer composition includes a step of deprotecting the protected carboxylic acid group for obtaining a polymerizable polymer. In a further preferred embodiment, the aqueous dental glass ionomer composition includes a step of deprotecting the protected carboxylic acid group after step b).

The conditions for deprotection of an optionally protected carboxyl group are selected according to the protecting group used. Preferably, the protected carboxyl group is deprotected by hydrogenolysis or treatment with acid or base.

The polymerizable polymer according to (B) may be the same as disclosed in EP 3106146 A1 or EP 3231412 A2.

The polymerizable polymer according to (B) preferably has an average molecular weight $M_w$ in the range of from $10^3$, in particular $10^4$ to $10^6$ Da. More preferably, the average molecular weight $M_w$ is in the range of from $10^5$ to $7 \cdot 10^5$ Da, or $3 \cdot 10^4$ to $2.5 \cdot 10^5$ Da.

The polymerizable polymers according to (B) must be sufficient in number or percent by weight of carboxylic acid groups to bring about the setting or curing reaction in the presence of the reactive particulate glass according to (A) or any further unmodified or modified particulate reactive(s) and/or non-reactive filler(s). Preferably, the polymerizable polymer according to (B) is present in the aqueous dental glass ionomer composition in an amount of from 5 to 80 percent by weight, more preferably 10 to 50 percent by weight, still more preferably 15 to 40 percent by weight, based on the total weight of the composition.

As a polymerization initiator system according to (D), any compound or system, capable of initiating the copolymerization reaction according to the present invention may be suitably used. The polymerization initiator according to (D) may be a photoinitiator or a redox initiator or a mixture thereof.

A suitable redox initiator comprises an reducing and oxidizing agents, which typically react with or otherwise cooperate with one another to produce free-radicals capable of initiating polymerization of polymerizable double bonds in components (B) and (C) in a dark reaction, independent from the presence of light. The reducing and oxidizing agents are selected so that the polymerization initiator system is sufficiently storage-stable and free of undesirable colorization to permit storage and use under typical dental conditions. Moreover, the reducing and oxidizing agents are selected so that the polymerization initiator system is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the polymerization initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

Suitable photoinitiators for polymerizing free radically photopolymerizable compositions may include binary and tertiary systems. Tertiary photoinitiators may include an iodonium salt, a photosensitizer, and an electron donor compound as described in U.S. Pat. No. 5,545,676. Suitable iodonium salts include the diaryl iodonium salts, e.g., diphenyliodonium chloride, diphenyliodonium hexafluorophosphate, diphenyl-iodonium tetrafluoroborate, and tolylcumyliodonium tetrakis(pentafluorophenyl)borate. Suitable photosensitizers are monoketones and diketones that absorb some light within a range of about 400 nm to about 520 nm (preferably, about 450 nm to about 500 nm).

Particularly suitable compounds include alpha diketones that have some light absorption within a range of about 400 nm to about 520 nm (even more preferably, about 450 to about 500 nm). Examples include camphorquinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate.

Suitable photoinitiators may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dinnethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

The amount of active species of the polymerization initiator is not particularly limited. Suitably, the amount of polymerization initiator in the polymerization system according to (D) is in the range of from 0.001 to 5 mol % based on the total amount of the monomers.

The aqueous dental glass ionomer composition is a curable dental composition, that is a cured dental glass ionomer composition/cement can be obtained therefrom by polymerizing the polymerizable polymer according to (B) and the monomer according to (C) in the presence of the reactive particulate glass (A) and the polymerization initiator system according to (D).

Preferably, the present dental glass ionomer composition has an adhesive bond strength to dentin is of at least 5 MPa as measured according to ISO 29022:2013; and/or a flexural strength is of at least 80 MPa as measured according to ISO 4049.

Hereinafter, the present invention will be described in further detail with the reference to examples. The present invention is not limited to the examples described below.

EXAMPLES

Synthesis Example 1

Synthesis of 3-{Acryloyl-[3-(Acryloyl-Ethyl-Amino)-Propyl]-Amino}-Propionic Acid (ABADEP1)

Step 1: Synthesis of N-[3-(Benzyl-Ethyl-Amino)-Propyl]Phthalimide

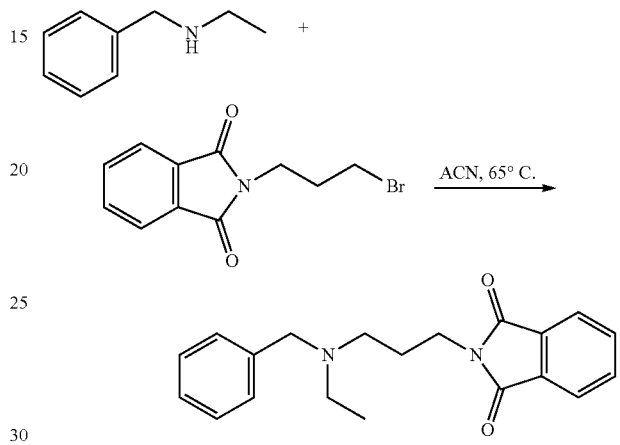

20 g of N-ethylbenzylamine were solved in acetonitrile. 1.5 equivalents of potassium carbonate were added. The mixture was stirred at room temperature. 1.0 Equivalent of N-(3-Brompropyl)-phthalimde were solved in acetonitrile and added to the mixture. The mixture was stirred at 65° C. for 24 h and afterwards cooled down. The substance was filtered and the solvent was removed under vacuum at 40° C. Yield: 90%

Step 2: Synthese Von $N^1$-Benzyl-$N^1$-Ethyl-Propane-1,3-Diamine

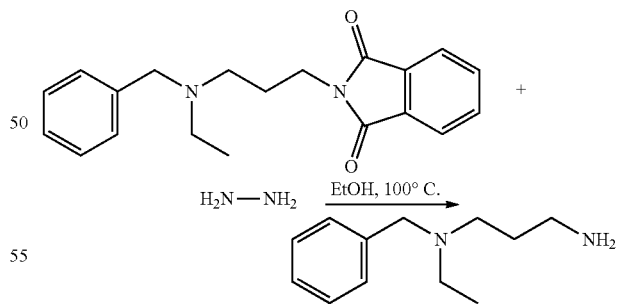

42.9 g of step 1 was solved in ethanol. 4.5 equivalent of hydrazine monohydrate was added. The mixture was stirred at 100° C. for 2.5 h and afterwards cooled down. The substance was filtered and the solvent was removed under vacuum at 40° C. The residue was solved in water and the water phase was extracted with dichloromethane. The organic phase was washed with NaCl-solution and dried over sodium sulfate. The solvent was removed under vacuum at 40° C. Yield: 94%

Step 3: Synthesis of 3-[3-(Benzyl-Ethyl-Amino)-Propylamino]-Propionic Acid-Tert-Butyl-Ester

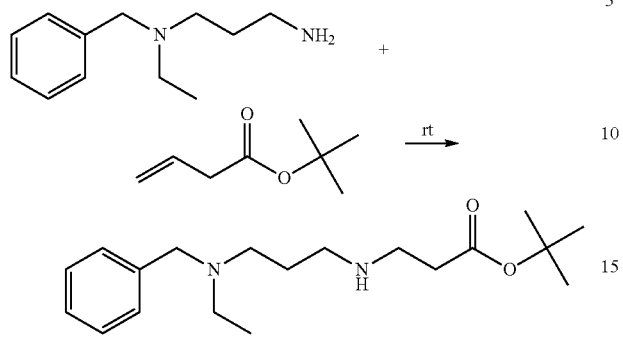

24 g of step 3 were added to 1 equivalent of t-butyl acrylate. The mixture was stirred at room temperature for 24 h. The product was purified by column chromatography. Yield: 77%

Step 4: Synthesis of 3-(3-Ethylamino-Propylamino)-Propionic Acid-Tert-Butylester

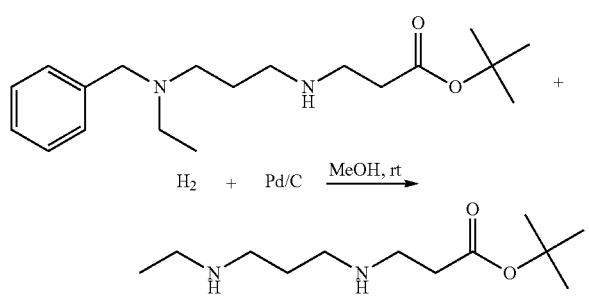

20.5 g of step 3 were solved in methanol. A catalytic amount of palladium/active coal were added. The mixture was stirred for 24 h under hydrogen. The product was filtered and washed with methanol. The solvent was removed under vacuum at 40° C. Yield: 96%

Step 5: Synthesis of 3-{Acryloyl-[3-(Acryloyl-Ethyl-Amino)-Propyl]-Amino}Propionic Acid-Tert-Butylester

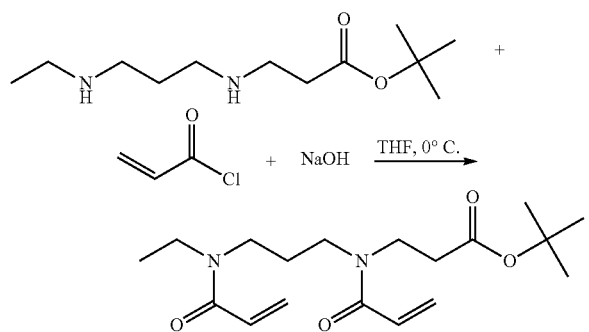

11.5 g of step 4 were solved in THF. 3.4 equivalents sodium hydroxide were solved in water and added to the THF solution. The mixture was cooled down and 2 equivalents of acryoyl chloride in THF were added slowly. The mixture was stirred for 5 h under ice cooling. The solvent was removed under vacuum at 40° C. The product was solved in water and extracted with ethyl acetate. The organic phase was successively washed with HCl—, NaHCO$_3$-solution and NaCl-solution and dried over sodium sulfate. The solvent was removed under vacuum at 40° C. The product was purified by column chromatography. Yield: 74%

Step 6: Synthesis of 3-{Acryloyl-[3-(Acryloyl-Ethyl-Amino)-Propyl]Amino}-Propionic Acid

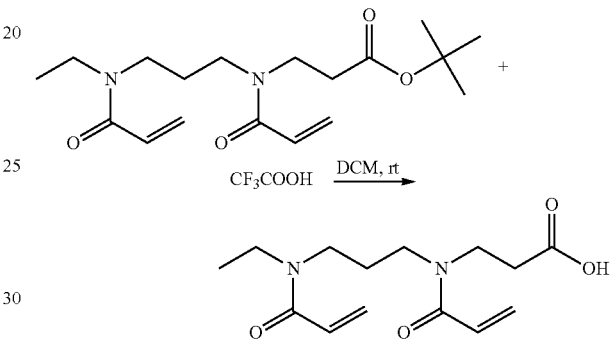

1.4 g of step 5 were mixed with dichloromethane. 2 mL of trifluoroacetic acid were added and the mixture was stirred at room temperature for 4 h. The solvent was removed under vacuum at 40° C. The product was solved in dichloromethane and washed with water. The organic phase was washed with NaCl-solution dried over sodium sulfate. The solvent was removed under vacuum at 40° C. Yield: 60%

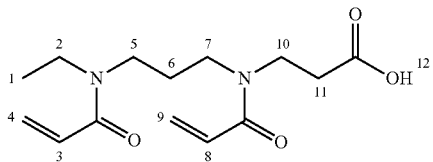 [SMILES: C=CC(=O)N(CC)CCCN(CCC(=O)O)C(=O)C=C]

1H NMR [300 MHz, CDCl$_3$]: δ 9.19 (H-12, 1H, sb); δ 6.47-6.63 (H-3/H-8, 2H, m); δ 6.34-6.30 (H-4a/H-12a, 2H, m); δ 5.71 (H-4b/H-12b, 2H, m); δ 3.70-3.62 (H-4b/H-12b, 2H, m); δ 3.46-3.33 (H-4a/H-5/H-7/H-12a, m); δ 2.68-2.60 (H-11, 2H, m); δ 1.87 (H-6, 2H, m), δ 1.23-1.11 (H-1, 3H, t)

Application Example 1 and Comparative Example 1

Aqueous dental glass ionomer compositions of Example 1 according to the invention and of the Comparative Example 1 have been prepared by forming a liquid and a powder composition of the ingredients listed in Table 1 below, which respectively add up to 100 wt %, and admixing both parts in the shown powder/liquid (P/L) ratio.

Curing Time

Working time: Period of time, measured from the start of mixing the powder and glass in the shown P/L ratio, during which it is possible to manipulate the material without an adverse effect on the properties.

Setting time: Point of time at which the mixture stopped being deformed even under pressing.

Flexural Strength/E-Modulus

The obtained dental glass ionomer compositions of Example 1-5 and Comparative Example 1-3 were filled in a stainless steel mould having the size (25±2) mm×(2.0±0.1) mm×(2.0±0.1) mm, for the preparation of test specimens. The thus obtained dental glass ionomer compositions were cured with a dental curing light (light-cured, LC) as well as without external power source (self-cured, SC). For the resulting cured dental glass ionomer composition, the flexural strength has been determined according to ISO 4049.

TABLE 1

|  |  | Example 1 |  | Comparative Example 1 |  |
|---|---|---|---|---|---|
| Liquid | Water | 34.3 |  | 34.3 |  |
|  | Cross-linker | 0 |  | 15 |  |
|  | ABADEP 1 | 15.0 |  | 0 |  |
|  | Modified polyacid | 25.0 |  | 25 |  |
|  | Acrylic acid | 25.4 |  | 25.4 |  |
|  | Photopolymerization system + Inhibitor | 0.3 |  | 0.3 |  |
|  | Σ | 100 |  | 100 |  |
| Powder | Reactive glass mixture | 99.4 |  | 99.4 |  |
|  | Redox curing system | 0.6 |  | 0.6 |  |
|  | Σ | 100 |  | 100 |  |
| P/L ratio |  | 3.0 |  | 3.0 |  |
| Curing time | Working time (seconds) | 180 | SAH02-063-01 | 200 | SKA17-162-02 |
|  | Setting time (seconds) | 220 | SAH02-063-02 | 240 | SKA17-162-01 |
| Flexural strength (SC) [MPa] |  | 94 ± 5 | SAH 02-060-01 D | 99 ± 8 | SAH02-033-03 |
| Flexural strength (LC) [MPa] |  | 95 ± 16 | SAH 02-060-01 C | 92 ± 5 | SKA17-161-02 |
| E-Modulus (SC) [MPa] |  | 13500 ± 430 | SAH 02-060-01 D | 10900 ± 320 | SAH02-033-03 |
| E-Modulus (LC) [MPa] |  | 13700 ± 260 | SAH 02-060-01 C | 11200 ± 340 | SKA17-161-02 |

The invention claimed is:

1. A dental composition comprising a polymerizable acidic compound of the following formula (I):

$$\left[H_2C \overset{R^1}{=} \overset{}{\underset{O}{C}} - \overset{R^2}{\underset{}{N}} \right]_m L \left[ \overset{R^3}{\underset{}{N}} - \overset{}{\underset{O}{C}} \overset{R^1}{=} CH_2 \right]_n \quad (I)$$

wherein
$R^1$ which may be the same or different when more than one $R^1$ is present, represents a hydrogen atom or a methyl group;
$R^2$ which may be the same or different when more than one $R^2$ is present, represents a hydrogen atom, a straight-chain or branched $C_{1-6}$ alkyl group, a $C_{3-8}$ cycloalkyl group or a straight-chain or branched $C_{2-6}$ alkenyl group;
$R^3$ which may be the same or different when more than one $R^3$ is present, represents a monovalent organic moiety substituted by a group —COOM, wherein M independently represents a hydrogen atom or a metal atom or
$R^2$ and $R^3$
form together a divalent organic moiety substituted by a group selected from —COOM, —PO$_3$M, —O—PO$_3$M$_2$ and —SO$_3$M, wherein M independently represents a hydrogen atom or a metal atom;
L represents a (m+n+1)-valent organic linker group;
X represents a hydrogen atom or a group selected from —COOM, —PO$_3$M, —O—POM$_2$ or —SO$_3$M, wherein M independently is a hydrogen atom or a metal atom;
m is an integer of 0 to 6;
n is an integer of 1 to 6;
wherein (m+n) is at least 2.

2. The dental composition according to claim 1, wherein m is 1.

3. The dental composition according to claim 1, wherein n is 1.

4. The dental composition according to claim 1, wherein $R^3$ is a group of the following formula (II):

$$\left. \begin{array}{c} R^5 \\ | \\ -C- \\ | \\ R^4 \end{array} \right]_a [Y]_b \left. \begin{array}{c} R^6 \\ | \\ -C- \\ | \\ R^7 \end{array} \right]_c -Z \quad (II)$$

wherein
$R^4$ which may be the same or different when more than one $R^4$ is present, represents a hydrogen atom or a $C_{1-4}$ alkyl group;
$R^5$ which may be the same or different when more than one $R^5$ is present, represents a hydrogen atom or a $C_{1-4}$ alkyl group;
$R^6$ which may be the same or different when more than one $R^6$ is present, represents a hydrogen atom or a $C_{1-4}$ alkyl group;
$R^7$ which may be the same or different when more than one $R^7$ is present, represents a hydrogen atom or a $C_{1-4}$ alkyl group;
Y represents an oxygen atom or a sulfur atom;
Z represents a group —COOM, wherein M independently is a hydrogen atom or a metal atom;
a is an integer of 1 to 6;
b is an integer of 0 or 1; and
c is an integer of 1 to 6.

5. The dental composition according to claim 1 wherein $R^1$ represents a hydrogen atom.

6. The dental composition according to claim 1, wherein $R^2$ represents a $C_{1-6}$ alkyl group, or a $C_{2-6}$ alkenyl group.

7. The dental composition according to claim 1, wherein L represents a (m+n+1)-valent aliphatic or alicyclic linker group.

8. The dental composition according to claim 1, wherein X represents a group selected from —COOM, —PO$_3$M, or —O—PO$_3$M$_2$, wherein M is a hydrogen atom.

9. The dental composition according to claim 4, wherein $R^4$, $R^5$, $R^6$, and $R^7$ represent a hydrogen atom.

10. The dental composition according to claim 4, wherein X is a hydrogen atom.

11. The dental composition according to claim 1, which further comprises a solvent and/or a particulate filler.

12. The dental composition according to claim 1, wherein the dental composition is a dental restorative or dental prosthetic composition.

13. The dental composition according to claim 1, wherein the dental composition is a dental adhesive composition, a dental composite composition, a resin modified dental cement, a pit and fissure sealer, a desensitizer or a varnish.

14. A method of preparing a dental composition comprising an aqueous resin modified dental glass ionomer composition; said method comprising:

(a) forming a liquid composition comprising water, a cross-linker, a water soluble polymer comprising acidic groups, a polymerizable acidic compound of the following formula (I):

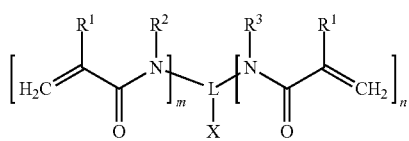

(I)

wherein $R^1$ which may be the same or different when more than one $R^1$ is present, represents a hydrogen atom or a methyl group;

$R^2$ which may be the same or different when more than one $R^2$ is present, represents a hydrogen atom, a straight-chain or branched $C_{1-6}$ alkyl group, a $C_{3-8}$ cycloalkyl group or a straight-chain or branched $C_{2-6}$ alkenyl group;

$R^3$ which may be the same or different when more than one $R^3$ is present, represents a monovalent organic moiety substituted by a group —COOM, wherein M independently represents a hydrogen atom or a metal atom; or $R^2$ and $R^3$
form together a divalent organic moiety substituted by a group selected from —COOM, —$PO_3M$, —O—$PO_3M_2$ and —$SO_3M$, wherein M independently represents a hydrogen atom or a metal atom;

L represents a (m+n+1)-valent organic linker group;

X represents a hydrogen atom or a group selected from —COOM, —$PO_3M$, —O—$PO_3M_2$ or —$SO_3M$, wherein M is a hydrogen atom or a metal atom;

m is an integer of 0 to 6;

n is an integer of 1 to 6;

wherein m+n is at least 2; and a polymerization initiator system;

(b) forming a powder composition comprising a reactive glass mixture and a redox curing system; and (c) admixing the liquid and the powder composition to form the aqueous resin modified dental glass ionomer composition.

\* \* \* \* \*